United States Patent
Kumasaka

(10) Patent No.: US 6,174,302 B1
(45) Date of Patent: Jan. 16, 2001

(54) DISPOSABLE DIAPER

(75) Inventor: Yoshinori Kumasaka, Kagawa-ken (JP)

(73) Assignee: Uni-Charm Corporation (JP)

( * ) Notice: Under 35 U.S.C. 154(b), the term of this patent shall be extended for 0 days.

(21) Appl. No.: 09/160,660

(22) Filed: Sep. 25, 1998

(30) Foreign Application Priority Data

Sep. 30, 1997 (JP) .................................................. 9-266186

(51) Int. Cl.$^7$ .................................................. A61F 13/15
(52) U.S. Cl. ................................ 604/385.28; 604/385.01; 604/385.04
(58) Field of Search ........................... 604/385.2, 385.01, 604/385.04, 385.28

(56) References Cited

U.S. PATENT DOCUMENTS

| | | | |
|---|---|---|---|
| H1630 | * 1/1997 | Roe et al. | 640/385.2 |
| 4,695,278 | 9/1987 | Lawson . | |
| 5,074,856 | * 12/1991 | Coe et al. | 604/385.1 |
| 5,304,159 | * 4/1994 | Tanji et al. | 604/385.2 |
| 5,304,160 | * 4/1994 | Igaue et al. | 604/385.2 |
| 5,342,342 | * 8/1994 | Kitaoka | 604/385.2 |
| 5,391,162 | * 2/1995 | Widlund et al. | 604/385.2 |
| 5,476,458 | * 12/1995 | Glaug et al. | 604/378 |
| 5,490,847 | * 2/1996 | Correa et al. | 604/387 |
| 5,577,540 | * 11/1996 | Sageser | 156/226 |
| 5,582,606 | * 12/1996 | Bruemmer et al. | 604/385.2 |
| 5,613,959 | * 3/1997 | Roessler et al. | 604/364 |
| 5,643,243 | * 7/1997 | Klemp | 604/385.2 |
| 5,643,244 | * 7/1997 | Yamaki et al. | 604/385.2 |
| 5,647,863 | * 7/1997 | Hammons et al. | 604/378 |
| 5,649,917 | * 7/1997 | Roberts et al. | 604/385.1 |
| 5,649,918 | * 7/1997 | Schleinz | 604/385.2 |
| 5,649,919 | * 7/1997 | Roessler et al. | 604/385.2 |
| 5,669,896 | * 9/1997 | Kielpikowski | 604/385.2 |
| 5,674,213 | * 10/1997 | Sauer | 604/385.1 |
| 5,707,364 | * 1/1998 | Coates | 604/391 |
| 5,718,698 | * 2/1998 | Dobrin et al. | 604/383 |
| 5,730,738 | * 3/1998 | McFall et al. | 604/387 |
| 5,746,732 | * 5/1998 | Olsson et al. | 604/385.2 |
| 5,752,947 | * 5/1998 | Awolin | 604/387 |
| 5,766,213 | * 6/1998 | Hackman et al. | 604/385.1 |
| 5,810,800 | * 9/1998 | Hunter et al. | 604/385.2 |
| 5,820,618 | * 10/1998 | Roberts et al. | 604/385.1 |
| 5,824,172 | * 10/1998 | Kielpikowski | 156/164 |
| 5,827,259 | * 10/1998 | Laux et al. | 604/385.2 |
| 5,851,204 | * 12/1998 | Mizutani | 604/385.2 |
| 5,911,713 | * 6/1999 | Yamada et al. | 604/385.2 |

FOREIGN PATENT DOCUMENTS

WO 95/14453    6/1995  (WO) .

* cited by examiner

Primary Examiner—John G. Weiss
Assistant Examiner—Paul Shanoski
(74) Attorney, Agent, or Firm—Baker & Daniels

(57) ABSTRACT

A disposable diaper includes a liquid-permeable topsheet, a liquid-impermeable backsheet and an absorbent core disposed therebetween. The core has its transversely opposite side edges curved inwardly of the core. Portions of the topsheet and the backsheet extending outward beyond the side edges of the core are put flat and bonded together. Such extensions are folded inwardly of the diaper along straight folding lines extending longitudinally outside the respective curved side edges of the core so as to form a pair of leak-proofing cuffs. First and second elastically stretchable/contractile members are bonded under appropriate tension to the respective leak-proofing cuffs along its inner side edges and the straight folding lines.

13 Claims, 2 Drawing Sheets

DISPOSABLE DIAPER

BACKGROUND OF THE INVENTION

This invention relates to disposable diapers for absorption and containment of urine and other body exudates.

Japanese Patent Application Disclosure (Kokai) No. Hei7-289584 discloses a disposable diaper including leak preventing cuffs normally biased to rise up on an inner surface of the diaper. These cuffs are composed of substantially crescent-shaped elastic sheets which extend longitudinally of the diaper and are bonded under tension along their arc-shaped edges to the inner surface of the diaper. Such an arrangement makes it possible to form the cuffs having their heights gradually decreasing from the maximal dimension in the crotch region to the minimal dimension in the proximity of the waist-opening. The diaper provided with such cuffs is not bulky in the proximity of the waist-opening and therefore convenient for wearing it.

With this known diaper, a main body of the diaper must be previously curved in order to bond the crescent-shaped cuffs to the main body. A step of bonding the cuffs to the main body previously curved in the corresponding shape inevitably obstructs a desired speed-up of production. In addition, use of an elastic sheet as material for these cuffs necessarily increases the material cost.

SUMMARY OF THE INVENTION

An object of the invention is to solve the problems encountered by the conventional diaper provided with the foregoing leakage proofing cuffs.

According to the invention, there is provided a disposable diaper comprising a main body serving for absorption of body fluids, the main body comprising, in turn, a liquid-permeable topsheet, a liquid-impermeable backsheet and a liquid-absorbent core disposed therebetween, and a pair of elastically stretchable/contractile leakage proofing cuffs formed along transversely opposite side edges of the main body, the leak preventing cuffs extending longitudinally of the diaper and being collapsed inwardly of the main body onto an inner surface thereof under an elastic bias to rise up the leakage proofing cuffs on the inner surface, wherein the core is defined by front and rear ends and opposite side edges, the side edges being curved inwardly of the core at least along longitudinally middle parts of the side edges, and each of the leakage proofing cuffs at least partially is formed by portions of the topsheet and the backsheet extending outward beyond transversely opposite side edges of the core and includes a lower portion extending in a region defined between the curved side edge of the core and a straight folding line extending longitudinally outside the curved side edge and an upper portion formed by folding an extension of the lower directed transversely of the main body along the straight folding line onto the inner surface of the main body, wherein elastically stretchable/contractile members are secured under appropriate tension to the leak preventing cuffs at least in the proximity of the folding line and in the proximity of an inner side edge of the upper portion extending in parallel to the folding line.

DESCRIPTION OF THE PREFERRED EMBODIMENTS

Details of a disposable diaper according to the invention will be more fully understood from the description given hereunder with reference to the accompanying drawings.

Figure 1:
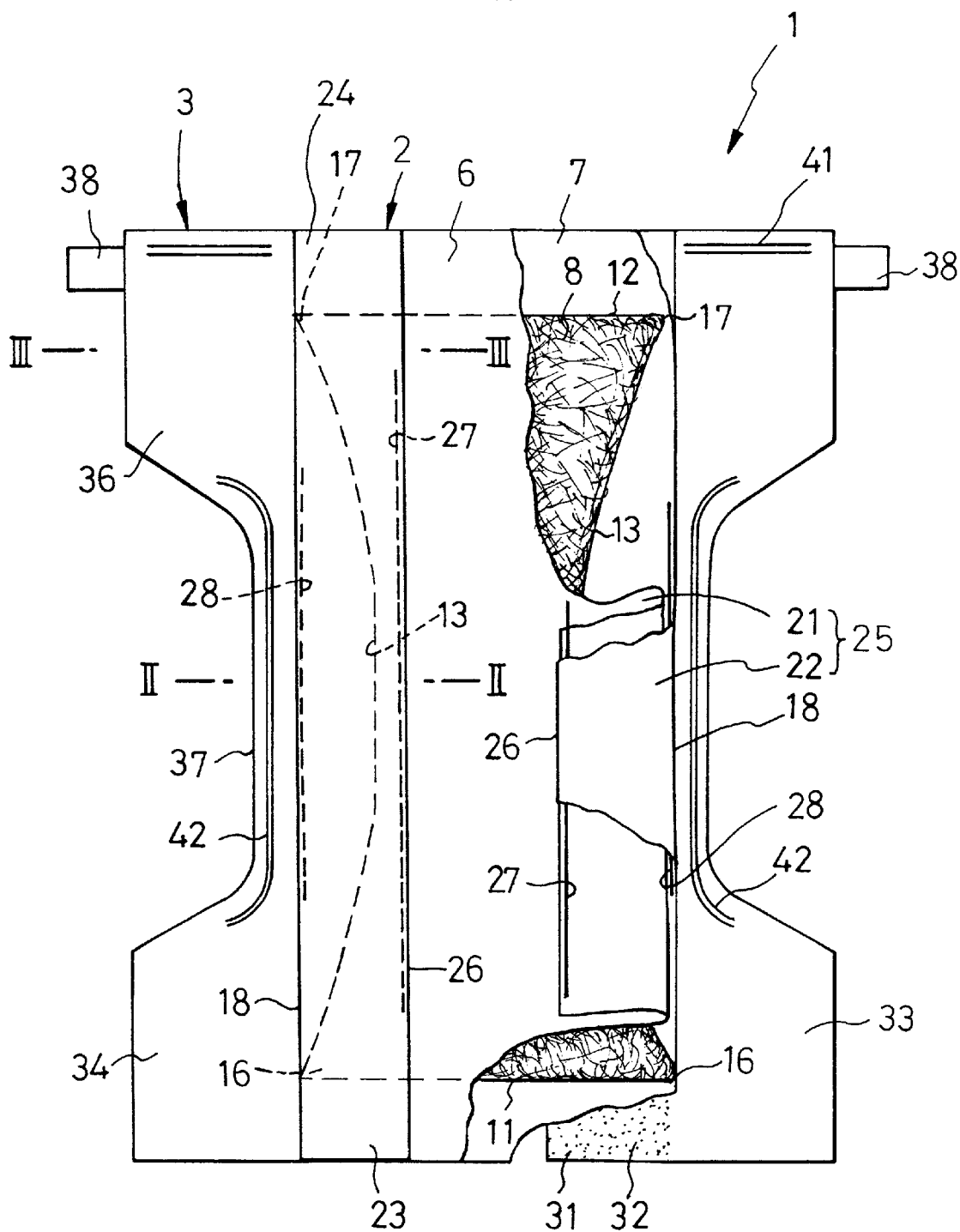
FIG. 1 is a plan view depicting a part cutaway diaper according to the invention.
Figure 2:
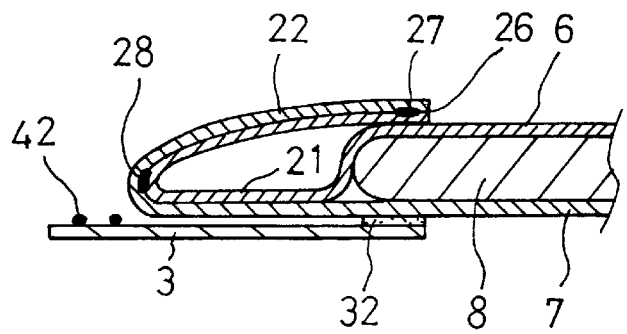
FIG. 2 is a sectional view taken along a line II—II in FIG. 1.
Figure 3:
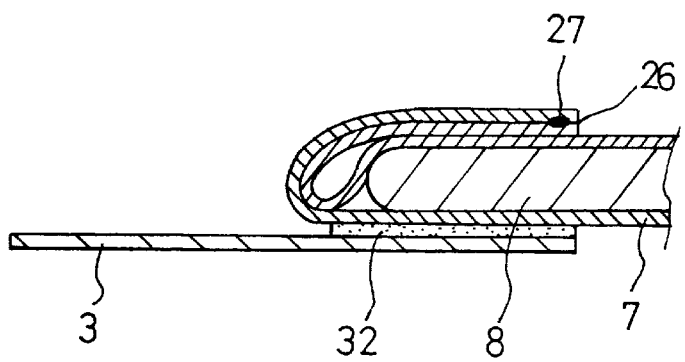
FIG. 3 is a sectional view taken along a line III—III in FIG. 1.

Referring to FIGS. 1, 2 and 3, a diaper 1 includes a main body 2 lying in the middle transversely thereof and a pair of side flaps 3 extending outward from transversely opposite side edges of the main body 2.

The main body 2 is composed of a liquid-permeable topsheet 6, a liquid-impermeable backsheet 7 and a liquid-absorbent core 8 disposed between these two sheets 6, 7. In FIG. 1, most of the core 8 is depicted with its outline by a broken line. As will be apparent from FIG. 1, the core 8 is defined by longitudinally opposite ends 11, 12 and transversely opposite side edges 13, 13 which are curved inwardly of the core 8. A distance between an imaginary straight line connecting longitudinally opposite ends 16, 17 of each side edge 13 and this side edge 13 is preferably dimensioned to be 5~40 mm at the middle of this side edge 13.

The topsheet 6 and the backsheet 7 extend outward beyond the ends 11, 12 and the side edges 13 of the core 8 and are put flat and bonded together by means of hot melt adhesive (not shown) along their extensions. The extensions of the topsheet 6 and the backsheet 7 bonded together in this manner are folded back along respective folding lines 18 defined by the foresaid imaginary lines connecting the longitudinally opposite ends 16, 17 of the respective side edges 13, 13 so that these extensions are collapsed toward an inner side of the main body 2 with the topsheet 6 lying inside. Thus a pair of leak preventing cuffs 25 are formed at transversely opposite side edges of the main body 2. Specifically, portions of these topsheet 6 and the backsheet 7 extending between the respective side edges 13 and the associated folding lines 18 define a pair of lower portions 21 of the leak preventing cuffs 25. Portions of the topsheet 6 and the backsheet 7 collapsed toward the main body 2 define upper portions 22 of the leak preventing cuffs 25. These lower and upper portions 21, 22 of the leak preventing cuffs 25 form together the pair of leak preventing cuffs 25 extending along longitudinally opposite side edges of the main body 2, respectively. Each of the upper portions 22 has its front and rear ends 23, 24 extending outward beyond the longitudinally opposite ends 11, 12 of the core 8 and bonded to the inner side of the main body 2 by means of suitable adhesive (not shown). The upper portions 22 have their inner side edges 26, 26 longitudinally extending in parallel to the respective folding lines 18.

Each of the leak preventing cuffs 25 including the lower and upper portions 21, 22 is provided with first and second elastically stretchable/contractile members 27, 28. The first elastically stretchable/contractile member 27 extends along the inner side edge 26 between the front and rear ends 23, 24. The second elastically stretchable/contractile member 28 extends along an intermediate part of the folding line 18 between the front and rear ends 23, 24 and is shorter than the first elastically stretchable/contractile member 27. These first and second elastically stretchable/contractile members 27, 28 are secured under appropriate tension to the inner surface(s) of the topsheet 6 or/and the backsheet 7. The first elastically stretchable/contractile members 27, 27 preferably extend in parallel to the respective inner side edges 26, 26.

On the other hand, it is not essential for the second elastically stretchable/contractile members 28 to extend in parallel to the respective folding lines 18. Specifically, the second elastically stretchable/contractile members 28 may be more or less curved or bent so long as they extend substantially along the respective folding lines 18 longitudinally of the leak preventing cuffs 25. It is also possible to form these second elastically stretchable/contractile members 28 by a plurality of elastically stretchable/contractile elements extending in parallel one to another, respectively.

The pair of side flaps 3 have their inner side edges 31, 31 bonded on their inner surfaces by means of hot melt adhesive 32 to an outer surface of the main body 2 in a region of the respective side flaps 3 defined between the respective side edges 13, 13 of the core 8, so that bonding of these flaps 3 may not restrict movement of the lower portion 21 of the leak preventing cuffs 25, in other words, since each of the lower portions 21 is not bonded to a region of the flaps 3 extending outward of the side edge 13, the lower portions 21 can move with respect to the flaps 3. Each of the flaps 3 are composed, in its remainder portion 33, of front and rear wings 34, 36 adapted to cover the wearer's waist regions and a notch 37 extending between the wings 34, 36 so as to surround the wearer's leg. Each of the rear wings 36 is provided with an elastically stretchable/contractile member 41 extending circumferentially of the wearer's waist regions and each of the notches 37 is provided with an elastically stretchable/contractile member 42 extending circumferentially of the wearer's leg. These elastically stretchable/contractile members 41, 42 are secured to the rear wings 36 and the notches 37, respectively, under appropriate tensions. These elastically stretchable/contractile members 41, 42 are depicted as they are exposed on an inner surface of the flap 3 and intended to come in contact with the wearer's skin. It should be understood, however, that the wearer's skin may be protected from direct contact with these elastically stretchable/contractile members 41, 42 by laminating two sheets to form the flap 3 and securing the members 41, 42 to an inner surface at least one of these two sheets. The rear wings 36 are provided in the proximity of their outer side edges with tape fasteners 38 adapted to be releasably anchored to outer surfaces of the respective front wings 34.

Figure 4:
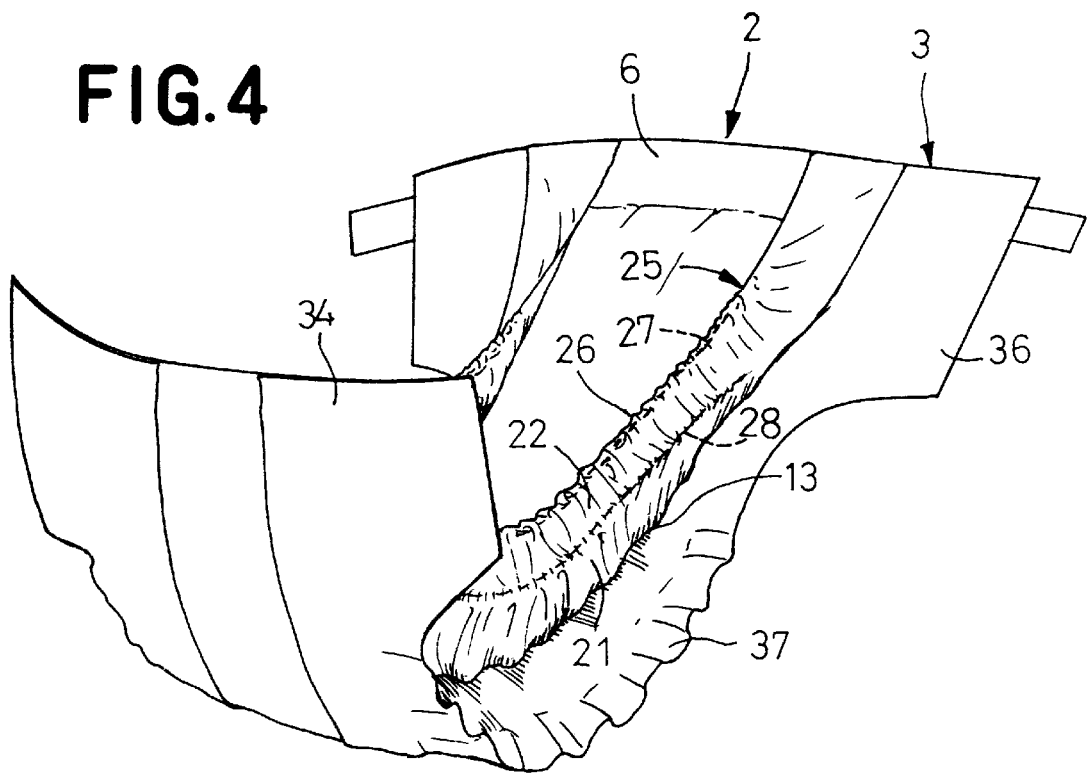
FIG. 4 is a perspective view depicting the diaper as being curved.

FIG. 4 is a perspective view depicting the posture the diaper of FIG. 1 takes when it is put on the wearer's body. As depicted, the diaper is curved longitudinally with the topsheet 6 lying inside. As the diaper is curved in this manner, the first and second elastically stretchable/contractile members 27, 28 contract, respectively. Consequently, the lower and upper portions 21, 22 of the leak preventing cuffs 25 rise up on the side edges 13 of the core 8 so as to be spaced from inner surfaces of the respective flaps 3 and the upper portions 22 rise up on the inner surface of the main body 2. In this way, the leak preventing cuffs 25 form relatively large leakage preventing walls each presenting a substantially crescent shape. In this posture, each of the leak preventing cuffs 25 has a height corresponding to a dimension from the associated side edge 13 of the core 8 to the inner side edge 26 of the associated upper portion 22. This dimension is maximum in the longitudinally middle region (crotch region) of the main body and gradually decreases toward the front and rear ends of the core 8. The leak preventing cuffs 25 of such an arrangement can effectively prevent a quantity of body fluids discharged on the diaper from leaking through a gap possibly formed between the wearer's body and the diaper when the diaper slips down along the wearer's body.

To implement the invention, a nonwoven fabric or a porous plastic sheet may be used to form the topsheet 6 and a plastic sheet may be used to form the backsheet 7. The core 8 may be formed by fluff pulp or a mixture of fluff pulp and polymer powder of high absorptivity. A nonwoven fabric, a plastic sheet or a laminate of them may be used to form the flaps 3. It is not important whether these materials for the flaps 3 is hydrophobic or hydrophilic so far as they are breathable and liquid-permeable. Bonding of the respective members may be achieved not only by using suitable adhesive such as hot melt adhesive but also by using a heat-sealing technique so long as the members to be bonded are of heat-sealable nature.

The leak preventing cuffs 25 depicted as the laminate of the topsheet 6 and the backsheet 7 may be implemented in the other various manners without departing from the scope of the invention. For example, regions of the respective leak preventing cuffs 25 extending in the proximity of the respective side edges 13, 13 of the core 8 may be formed by the topsheet 6 and the backsheet 7 laminated one upon another and the remainder regions may be formed by the backsheet 7 alone or replaced by waterproof sheets prepared separately of the topsheet 6 and the backsheet 7. Instead of separately preparing the pair of flaps 3 to be bonded to the main body 2 along its transversely opposite side edges, respectively, it is also possible to bond the main body 2 to an inner surface of a single hourglass-shaped sheet in its middle region and thereby to form the pair of flaps 3.

The disposable diaper includes a pair of leak preventing cuffs adapted to rise up on the inner surface of the diaper along the transversely opposite and inwardly curved side edges of the core. These leak preventing cuffs have their heights which are maximal in the crotch region and gradually decrease in the waist regions. The invention makes it unnecessary to prepare the leak preventing cuffs of such configuration separately of the main body as it has conventionally been the case and, in consequence, a corresponding increase in manufacturing cost due to such separately prepared members can be avoided.

What is claimed is:

1. A disposable diaper comprising:
    a main body for absorbing and containing body exudates, said main body including a liquid-permeable topsheet, a liquid-impermeable backsheet and a liquid-absorbent core disposed therebetween, said liquid-absorbent core having front and rear ends, a pair of opposite side edges that are curved inwardly at least along a longitudinal middle portion thereof;
    a pair of elastically stretchable/contractile leak preventing cuffs formed along transversely opposite side edges of said main body, said leak preventing cuffs extending longitudinally of said diaper and being collapsible inwardly of said main body onto an inner surface of said main body under an elastic bias which causes said leak preventing cuffs to rise up on the inner surface; and
    a pair of side flaps extending outward from transversely opposite side edges of said main body, each of said side flaps being provided with an elastically stretchable/contractile member extending longitudinally of said side flap,
    said liquid-absorbent core being defined by front and rear ends and a pair of opposite side edges, said side edges being curved inwardly at least along longitudinally middle portions thereof
    each of said leak preventing cuffs is at least partially formed by portions of at least one of said topsheet and said backsheet which extend outward beyond transversely opposite side edges of said core and includes a lower portion extending in a region defined between said side edge of said core and an outer fold line extending longitudinally outside said curved side edge of said core, each of said leak preventing cuffs further includes an upper portion formed by folding an extension of said lower portion directed transversely of said main body along said outer fold line onto said inner surface of said main body, wherein elastically stretchable/contractile members extending longitudinally of said main body are secured under tension to said leak preventing cuffs at least in the proximity of said outer fold line and in the proximity of an inner side edge of said upper portion extending in parallel to said outer fold line.

2. A disposable diaper according to claim 1, wherein each of said leak preventing cuffs is bonded at longitudinally opposite ends to said main body.

3. A disposable diaper according to claim 2, wherein said longitudinally opposite ends of said of said leak preventing cuffs are bonded onto the inner surface of said main body.

4. A disposable diaper according to claim 1, wherein each of said side flaps has an inner side edge surface portion bonded to an outer side edge surface of said main body in a region which lies beneath said liquid-absorbent core.

5. A disposable diaper comprising:
  a main body for absorbing and containing body exudates, said main body including a liquid-permeable topsheet, a liquid-impermeable backsheet and a liquid-absorbent core disposed therebetween, said liquid-absorbent core having front and rear ends, a pair of opposite side edges that are curved inwardly at least along a longitudinal middle portion thereof; and
  a pair of elastically stretchable/contractile leak preventing cuffs formed by portions of at least one of said topsheet and backsheet which extend outward beyond transversely said pair of opposite side edges of said liquid-absorbent core, said leak preventing cuffs being collapsible inwardly of said main body onto said topsheet under an elastic bias which causes said leak preventing cuffs to rise up on said topsheet, each of said leak preventing cuffs including a lower portion that extends in a region defined between said side edge of said liquid-absorbent core and an outer fold line that extends longitudinally outside said curved edge of said liquid-absorbent core and an upper portion formed by folding an extension of said lower portion transversely of said main body along said outer fold line onto said topsheet, wherein elastically stretchable/contractile members extend longitudinally of said main body and are secured under tension to said leak preventing cuff at least in proximity of said outer fold line and in proximity of an inner side edge of said upper portion extending in parallel to said outer fold line; and
  a pair of side flaps that extend outward from transversely opposite side edges of said main body, each of said side flaps being provided with an elastically stretchable/contractile member extending longitudinally of said side flap.

6. A disposable diaper according to claim 6 wherein each of said side flaps has an inner side edge surface joined to an outer side edge of said main body in a region which lies beneath said core.

7. A disposable diaper according to claim 6, wherein each of the leak preventing cuffs is bonded longitudinally opposite ends to said main body.

8. A disposable diaper according to claim 8, wherein said longitudinal opposite ends of said leak preventing cuffs are bonded onto the inner surface of said main body.

9. A disposable diaper comprising:
  a main body for absorbing and containing body exudates, said main body including a liquid-permeable topsheet, a liquid-impermeable backsheet and a liquid-absorbent core disposed therebetween, said liquid-absorbent core having front and rear ends, a pair of opposite side edges that are curved inwardly at least along a longitudinal middle portion thereof;
  a pair of elastically stretchable/contractile leak preventing cuffs formed along transversely opposite side edges of said main body, said leak preventing cuffs extending longitudinally of said diaper and being collapsible inwardly of said main body onto an inner surface of said main body under an elastic bias which causes said leak preventing cuffs to rise up on the inner surface; and
  a pair of side flaps extending outward from transversely opposite side edges of said main body and extending continuously across along a longitudinal length of the main body,
  said liquid-absorbent core being defined by front and rear ends and a pair of opposite side edges, said side edges being curved inwardly at least along longitudinally middle portions thereof,
  each of said leak preventing cuffs is at least partially formed by portions of at least one of said topsheet and said backsheet which extend outward beyond transversely opposite side edges of said core and includes a lower portion extending in a region defined between said side edge of said core and an outer fold line extending longitudinally outside said curved side edge of said core, each of said leak preventing cuffs further includes an upper portion formed by folding an extension of said lower portion directed transversely of said main body along said outer fold line onto said inner surface of said main body, wherein elastically stretchable/contractile members extending longitudinally of said main body are secured under tension to said leak preventing cuffs at least in the proximity of said outer fold line and in the proximity of an inner side edge of said upper portion extending in parallel to said outer fold line.

10. A disposable diaper according to claim 10, wherein each of the leak preventing cuffs is bonded at longitudinally opposite ends to said main body.

11. A disposable diaper according to claim 11, wherein said longitudinal opposite ends of said leak preventing cuffs are bonded onto the inner surface of said main body.

12. A disposable diaper according to claim 10, wherein said diaper further comprises a pair of side flaps extending outward from transversely opposite side edges of said main body, each of said flaps having an inner side edge surface portion bonded to an outer side edge surface of said main body in a region which lies beneath said core.

13. A disposable diaper according to claim 13, wherein each of said side flaps is provided with an elastically stretchable/contractile member extending longitudinally thereof.

* * * * *

UNITED STATES PATENT AND TRADEMARK OFFICE
CERTIFICATE OF CORRECTION

PATENT NO. : 6,174,302 B1
DATED : January 16, 2001
INVENTOR(S) : Yoshinori Kumasaka It is certified that error appears in the above-identified patent and that said Letters Patent is hereby corrected as shown below:

Claim 5,
Line 1, change "6" to -- 5 --

Claim 7,
Line 1, change "6" to -- 5 --

Claim 8,
Line 1, change "8" to -- 7 --

Claim 10,
Line 1, change "10" to -- 9 --

Claim 11,
Line 1, change "11" to -- 10 --

Claim 12,
Line 1, change "10" to -- 9 --

Claim 13,
Line 1, change "13" to -- 12 --

Signed and Sealed this

Twenty-third Day of October, 2001

Attest:

*Nicholas P. Godici*

NICHOLAS P. GODICI
*Attesting Officer*    *Acting Director of the United States Patent and Trademark Office*